US007300771B2

(12) United States Patent
White et al.

(10) Patent No.: US 7,300,771 B2
(45) Date of Patent: Nov. 27, 2007

(54) PROCESS TO PRODUCE 19-NOR-10β-CARBOXYLIC ACIDS BY FUNGAL OXIDATION OF 6-SUBSTITUTED-Δ6-PREGNANES

(75) Inventors: Michael Jon White, Portage, MI (US); Ivan Gale Gilbert, Kalamazoo, MI (US); Bruce Allen Pearlman, Kalamazoo, MI (US)

(73) Assignee: Pfizer Inc., New York, NY (US)

( * ) Notice: Subject to any disclaimer, the term of this patent is extended or adjusted under 35 U.S.C. 154(b) by 388 days.

(21) Appl. No.: 10/760,785

(22) Filed: Jan. 20, 2004

(65) Prior Publication Data

US 2004/0175784 A1 Sep. 9, 2004

Related U.S. Application Data

(60) Provisional application No. 60/441,542, filed on Jan. 21, 2003.

(51) Int. Cl.
*C12P 33/00* (2006.01)
*C12P 7/40* (2006.01)
*C12P 1/02* (2006.01)

(52) U.S. Cl. .................. 435/52; 435/136; 435/171
(58) Field of Classification Search ................ 435/52, 435/136, 171; 552/604, 608
See application file for complete search history.

(56) References Cited

U.S. PATENT DOCUMENTS 3,039,926 A    6/1962  Shull ........................ 167/65
3,250,792 A *  5/1966  Wieland et al. ............. 552/592
3,475,275 A   10/1969  Shirasaka et al. ............ 195/51
4,284,720 A    8/1981  Petzoldt ....................... 435/58
4,560,656 A * 12/1985  Farbood et al. ............. 435/146

FOREIGN PATENT DOCUMENTS

FR    1 281 867 A    1/1962
FR    1 586 869 A    3/1970
JP    01 228497 A    9/1989

OTHER PUBLICATIONS

Schwarz et al. "Steroid derivatives. LXVI. Synthesis of 17 alpha-acetoxy-16-methylene analogs of 19-norprogesterons" Collection Czechoslovak Chem Comm. (1970) 35(5): 1536-1546, abstract only from CAS: 1970: 415087.*
CAS abstract 1963: 441936 for US 3250792.*
Sikyta, B. Methods in Industrial Microbiology. (1983) translated by Sigler, K. (Ellis Horwood Limited: Chichester, England), pp. 168-169.*
K. E. Smith, et al., *Journal of Steroid Biochemistry*, Microbial Transformations of Steroids-IV. 6, 7-Dehydrogenation; A New Class of Fungal Steroid Transformation Product, 33(2):271-276, XP-002278184 (1989).

* cited by examiner

*Primary Examiner*—Leon B. Lankford, Jr.
*Assistant Examiner*—Susan Hanley
(74) *Attorney, Agent, or Firm*—Gregg C. Benson; Robert T. Ronau; Lyman H. Smith

(57) ABSTRACT

A process to produce 19-nor-10β-carboxylic acids by fungal oxidation of 6-substituted-Δ6-pregnanes is disclosed.

11 Claims, No Drawings

PROCESS TO PRODUCE 19-NOR-10β-CARBOXYLIC ACIDS BY FUNGAL OXIDATION OF 6-SUBSTITUTED-Δ6-PREGNANES

CROSS REFERENCE TO RELATED APPLICATION

This application claims the benefit of U.S. provisional application Ser. No. 60/441,542 filed on 21 Jan. 2003, under 35 USC 119(e)(i), which are incorporated herein by reference in their entirety.

FIELD OF THE INVENTION

The present invention relates to the fungal oxidation of 6-substituted-$\Delta^6$-pregnanes of Formula I to form 19-nor-10β-carboxylic acids of Formula II, followed a chemical decarboxylation step to produce 19-nor-6-substituted-$\Delta^6$-pregnanes of Formula III.

BACKGROUND OF THE INVENTION

19-Nor 4,6-pregnadien-6-methyl-17α-ol-3,20-dione (nomegestrol) and the related molecules of Formula III are useful steroid intermediates for the synthesis of pharmacologically active 19-nor steroids. For example, 19-nor-4,6-pregnadien-6-methyl-17α-ol-3,20-dione (nomegestrol) can be used to synthesize nomegestrol acetate (19-nor-4,6-pregnadien-6-methyl-17α-ol-3,20-dione 17 acetate), a women's health steroid.

U.S. Pat. No. 4,284,720 discloses that 10-methyl steroids of the andostane or pregnane series are converted to the corresponding 19 hydroxy steroids by fermentation with a fungal culture of the genus *Nigrospora*.

19-Nor steroids have been chemically synthesized from 19-hydroxy steroids.

SUMMARY OF INVENTION

In general, the present invention provides a practical method for the fungal oxidation of 6-substituted-$\Delta^6$-pregnanes of Formula I to form 19-nor-10β-carboxylic acids of Formula II, followed a chemical decarboxylation step to produce 19-nor-6-substituted-$\Delta^6$-pregnanes of Formula III.

A process for the production of a 19-nor-10β-carboxylic acid of Formula II

Formula II wherein:
$R_1$ is selected from the group consisting of H, OH, R—C(O)O—, —$CH_2OCH_3$, $CH_3CH(OR)O$—;
R is a $C_1$-$C_8$ alkyl group;
$R_2$ is selected from H, F, Cl, Br, and $CH_3$—;
$R_3$, is H, or $CH_2$=;
$R_4$ is —$CH_2OH$ or —$CH_3$,
by fungal oxidation of a 6-substituted-$\Delta$6-pregnane of Formula I Formula I wherein
$R_1$ is selected from the group consisting of H, OH, R—C(O)O—, —$CH_2OCH_3$, $CH_3CH(OR)O$—;
R is a $C_1$-$C_8$ alkyl group;
$R_2$ is selected from H, F, Cl, Br, and $CH_3$—;
$R_3$, is H, or $CH_2$=;
$R_4$ is —$CH_2OH$ or —$CH_3$,
$R_5$ is —CHO, —$CH_2OH$ or $CH_3$
comprising:
contacting a 6-substituted-Δ6-pregnane of Formula I with a bioconversion culture containing a species of the genus *Nigrospora* capable of oxidizing the 19 carbon of a 6-substituted-$\Delta^6$-pregnane of Formula I.

DEFINITIONS

The definitions and explanations below are for the terms as used throughout this entire document including both the specification and the claims.

All temperatures are in degrees Celsius.

"r.p.m." refers to revolutions per minute.

"TLC" refers to thin-layer chromatography.

"HPLC" refers to high pressure liquid chromatography.

"psig" refers to pounds per square inch gage.

"RO" refers to reverse osmosis.

When solvent mixtures are used, the ratios of solvents used are volume/volume (v/v).

When the solubility of a solid in a solvent is used the ratio of the solid to the solvent is weight/volume (wt/v).

DETAILED DESCRIPTION OF THE INVENTION

In general, the invention relates to a fungal oxidation of 6-substituted-$\Delta^6$-pregnanes of Formula I

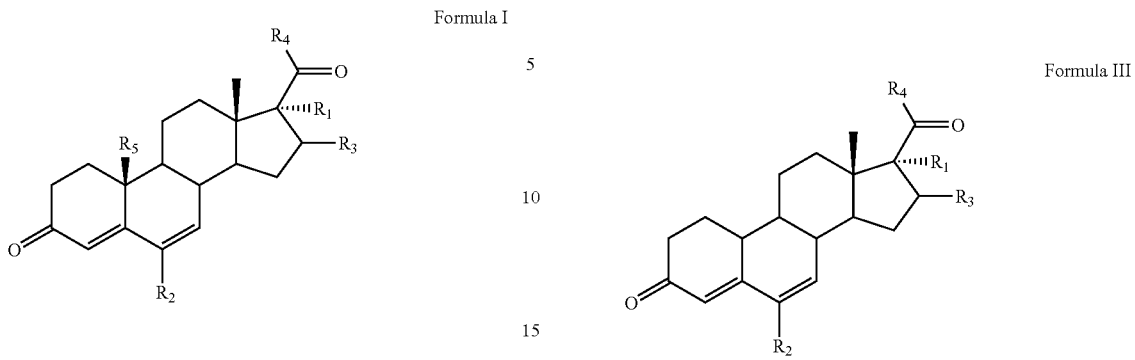

Formula I wherein
$R_1$ is selected from the group consisting of H, OH, R—C(O)O—, —$CH_2OCH_3$, $CH_3CH(OR)O$—;
R is a $C_1$-$C_8$ alkyl group;
$R_2$ is selected from H, F, Cl, Br, and $CH_3$—;
$R_3$, is H, or $CH_2$=;
$R_4$ is —$CH_2OH$ or —$CH_3$,
$R_5$ is —CHO, —$CH_2OH$ or $CH_3$,
to produce 19-nor-10β-carboxylic acids of Formula II.

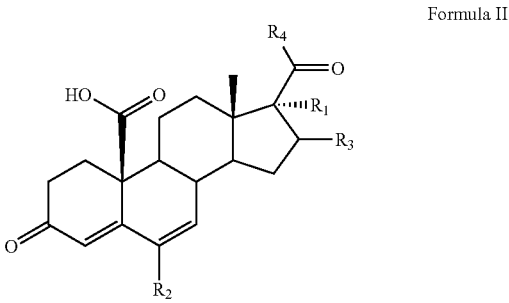

Formula II wherein, R, $R_1$, $R_2$, $R_3$, $R_4$, are the same as R, $R_1$, $R_2$, $R_3$, $R_4$, in Formula I.

Any filamentous fungus of the genus *Nigrospora* capable of oxidizing the 19 carbon of 6-substituted-Δ6-pregnanes of Formula I, may be used to produce 19-nor-10β-carboxylic acids of Formula II. The procedure of Example 1 can be used to determine whether a particular filamentous fungus of the genus *Nigrospora* is capable of oxidizing the 19 carbon of 6-substituted-$Δ^6$-pregnanes of Formula I.

The 19-nor-10β-carboxylic acids of Formula II may be subsequently recovered and chemically decarboxylated to produce 19-nor-6-substituted-$Δ^6$-pregnanes of Formula III.

Formula III wherein, R, $R_1$, $R_2$, $R_3$, $R_4$, are the same as R, $R_1$, $R_2$, $R_3$, $R_4$, in Formula I.

We have found that contacting 6-substituted-$Δ^6$-pregnanes of Formula I with certain strains of *Nigrospora*, particularly *Nigrospora sphaerica* ATCC 12772, *Nigrospora gorlenkoanum* ATCC 24718, and *Nigrospora oryzae* ATCC 42775 produced 19-nor-10β-carboxylic acids of Formula II.

In the process of the present invention the bioconversion medium contains a surfactant and a high level of carbon source. The surfactant is selected from the group of non-ionic detergents including non-ionic amides, nonionic esters such as ethoxylated alkyl phenols and polyoxyethylene sorbitan esters, emulsifying waxes, non-ionic ethoxylates, tristyrylphenol ethoxylates, alcohol ethoxylates such as octylphenoxypolyethoxyethanol, ethoxylated mercaptans, capped ethoxylates, block copolymers, and reverse copolymers. Preferably, ethoxylated alkyl phenols, polyoxyethylene sorbitan esters, or octylphenoxypolyethoxyethanol are used as surfactants. The non-ionic detergent concentration used may be from about 0.1 mL/L or 0.1 g/L to about 4 ml/L or 4 g/L, but typically about 1 mL/L or 1 g/L to about 2 mL/L or 2 g/L.

The carbon source is selected from the groups consisting of monosaccharides, disaccharides, trisaccharides, hydrolysed polysaccharides, and sugar alcohols. Typically, glucose is used as the carbon source. The concentration of carbon source may be from about 2 g/L to about 100 g/L, but typically about 5 g/L to about 60 g/L.

Preferably the fungus is grown in submerged culture under aerobic conditions, using any art-recognized procedure, and the oxidative reaction performed in situ. The desired *Nigrospora*, fungus is cultured using conditions, methods, carbon sources, and nitrogen sources known to those skilled in the art. Generally a primary and secondary vegetative seed procedure is used in preparation for the fungal 19-oxidation. Alternatively, a primary vegetative seed can be used directly to inoculate bioconversion media for the fungal 19-oxidation.

Primary vegetative seed cultures are incubated for a period of about 24 to about 96 hours (preferably about 48-72 hours) at a temperature between about 20° and about 37°

(preferably about 28°), and a pH between about 3.0 and about 7.5. Secondary vegetative seed medium is inoculated with about 0.006% to about 0.25% [v/v] primary vegetative seed culture, but typically about 0.012% to about 0.1% [v/v], and incubated for a period of about 36 to about 72 hours (preferably about 48-60 hours) at a temperature between about 20° and about 37° (preferably about 28°). The pH of the secondary seed medium can be between about 3.0 and about 7.5, but preferably between about 5.0 and about 7.0. The bioconversion medium, which can be the same or similar to the secondary vegetative seed medium, is inoculated with about 1% to about 10% [v/v] secondary vegetative seed culture (preferably about 3% to about 5%). After an initial incubation period of about 12 to about 72 hours (preferably about 16 to about 24 hours), steroid substrates of Formula I, preferably micronized, are added to the bioconversion culture. Micronized steroid substrates of Formula I can be added as a dry powder or an aqueous slurry, either as a single addition, a series of additions, or a continual feed. It is preferred to use the micronized steroid substrates of Formula I at a concentration greater than 1 g/L, more preferably greater than 2 g/L, even more preferably greater than 4 g/L. Bioconversion of steroid substrates of Formula I to form 19-oxidized products of Formula II, is allowed to proceed for between about 1 and about 9 days, but typically about 2 to about 6 days. The conversion may be monitored by a chromatographic method such as HPLC, known to those skilled in the art. A suitable HPLC method is provided in example 1.

Once the bioconversion of steroid substrates of Formula I to the 19-oxidative products of Formula II is complete, compounds of Formula II can be recovered using any one of a number of art-recognized procedures. Preferably, whole, or filtered, beer is extracted with a water-immiscible organic solvent, such as methylene chloride, by adjusting the pH downward until the product of Formula II is in the acid form. The water-immiscible organic solvent is then concentrated by evaporation. The product of Formula II is then extracted into water by adjusting the pH upwards until the carboxylic acid product of Formula II is ionized (pH 8 to 9). This aqueous extract is diluted with a water-miscible solvent, such as methanol, and the pH is adjusted downward until the product of Formula II is again in the acid form (pH 3 to 4). Crude product of Formula II is slowly crystallized by evaporation of the water-miscible solvent.

Steroid compounds of Formula II may be chemically decarboxylated to produce steroid compounds of Formula III. The decarboxylation step is performed using conditions and reagents as are known to those skilled in the art. Generally, compounds of Formula II are dissolved in a polar solvent, along with an acid catalyst. The mixture is heated to produce the desired decarboxylation. Typically, the carboxylic acid is treated with a catalytic amount of hydrochloric acid in aqueous methanol at reflux for about 30 minutes to effect the desired decarboxylation. However, the solvent and acid are not critical. Any solvent that will dissolve both the carboxylic acid substrate and the acid catalyst is suitable. Preferred solvents include pyridine, picoline, dimethyl sulfoxide (DMSO), hexmethyphosphoramide (HMPA), Sulfolane, dimethyl formamide, dimethyl acetamide, N-methylpyrrolidone, acetonitrile, acetone, methanol, ethanol, n-propanol, iso-propanol, or aqueous mixtures thereof. Methanol is the most preferred solvent. Compounds of Formula II are dissolved at a concentration of between about 10 mg/mL to about 500 mg/mL (preferably about 100-300 mg/mL).

A suitable acid catalyst is an acid that has a pKa less than 4.9. Such acids include hydrochloric acid, hydrobromic acid, sulfuric acid, glacial acetic acid, phosphoric acid, benzenesulfonic acid, bromoacetic acid, chloroacetic acid, citric acid, dichloroacetic acid, oxalic acid, trifluoroacetic acid, and trichloroacetic acid. The final concentration of the acid in methanol is between 0.001 N (pH 3) and 0.1 N (pH 1), preferably about 0.01 N (pH 2). The reaction mixture is heated to between 40° C. and 80° C. (preferably about 50-60° C.) for about 1 hour to about 24 hours (preferably 4 to 12 hours). Compounds of Formula III can be recovered from this reaction mixture using any one of a number of art-recognized procedures; the preferred procedure is crystallization by evaporative concentration and/or cooling.

The decarboxylation can also be accomplished in two steps: first, decarboxylation to give the 3-keto-$\Delta^{5(10)}$ intermediate, followed by the step of isomerization to compound (III). Decarboxylation to the 3-keto-$\Delta^{5(10)}$ intermediate can be effected by stirring in DMSO at room temperature (15-25° C.) for 16 hours. The 3-keto-$\Delta^{5(10)}$ intermediate is then isomerized to compound III by treatment with an acid of pKa less than 4.9 as described above.

EXAMPLES

Without further elaboration, it is believed that one skilled in the art can, using the preceding descriptions, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

Conversion of 4,6-pregnadien-6-methyl-17α-ol-3,20-dione to 19-nor-4,6-pregnadien6-methyl-17α-ol-3,20-dione 10β-carboxylic acid is performed using a submerged culture of *Nigrospora sphaerica* ATCC 12772, followed by decarboxylation to 19-nor 4,6-pregnadien-6-methyl-17α-ol-3,20-dione.

(A) Primary-Seed Stage

Frozen vegetative cells of *Nigrospora sphaerica* ATCC 12772 are thawed, transferred to potato-dextrose-agar plates (PDA), and incubated at 28° C. for 72 hours. Single mycelial-plugs (6-7 mm diam.) are used to inoculate siliconized 500-mL stippled shake flasks containing 100 mL primary-seed medium. Primary-seed medium consists of (per liter of RO water): dextrin, 50 g; soyflour, 35 g; glucose, 5 g; cobalt chloride hexahydrate, 2 mg; silicone defoamer (SAG 471), 0.5 mL; pre-sterilization pH 7.0-7.2, adjusted with sodium hydroxide (2N). Shake flasks, containing primary-seed medium, are sterilized for 30 minutes at 121° C. using an autoclave. *Nigrospora sphaerica* ATCC 12772 is incubated for 48 hours at 28° C., using a controlled-environment incubator-shaker set at 270 r.p.m. (2" orbital stroke).

(B) Secondary-Seed Stage

One hundred milliliter secondary-seed medium, in a siliconized 500 mL stippled shake flask, is inoculated using 0.2 mL of vegetative primary-seed culture 0.2% [v/v] inoculation rate). Secondary-seed medium contains (per liter of RO water): glucose, 30 g; soybean meal, 12.5 g; corn steep solids, 10 g; octylphenoxy polyethoxy ethanol, 0.25 mL; silicone defoamer (SAG 471), 0.5 mL; pre-sterilization pH 6.5-6.6, adjusted with sodium hydroxide (2N). Shake flasks, containing secondary-seed medium, are sterilized for 30 minutes at 121° C. using an autoclave. *Nigrospora sphaerica* ATCC 12772 is incubated for about 52 hours at 28° C., using a controlled-environment incubator-shaker set at 270 r.p.m. (2" orbital stroke).

(C) Steroid Bioconversion

One hundred milliliter steroid-bioconversion medium, in a siliconized 500 mL stippled shake flask, is inoculated using 5 mL vegetative secondary-seed culture (5% [v/v] inoculation rate). Steroid-bioconversion medium is essentially the same as the secondary-seed medium, with the exception that octylphenoxy polyethoxy ethanol is increased from 0.25 mL/L to 2 mL/L. At about 22 hours post-inoculation, 0.5 g micronized 4,6-pregnadien-6-methyl-17α-ol-3,20-dione slurried in a minimal volume of 0.2% [v/v] octylphenoxy polyethoxy ethanol is added to the 100-mL fermentation.

Bioconversion cultures are assayed on a daily basis for 19-nor-4,6-pregnadien-6-methyl-17α-ol-3,20-dione 10β-carboxylic acid using HPLC. One milliliter of whole beer is extracted with 3 mL warm acetonitrile. Cells are separated from the aqueous-acetonitrile mixture by centrifugation (3,000×g for 10 minutes), and 5 μL extract injected onto an HPLC column. Conditions for HPLC are as follows: Spectra-Physics chromatograph fitted with a C18 reverse-phase column (150×4.6 mm) column; column temperature, 30° C.; mobile phase (isocratic), acetonitrile/0.25% phosphoric acid (55/45, [v/v]); flow rate=0.5 mL/minute; detection, 287 nm; run time=20 minutes. Bioconversion of 4,6-pregnadien-6-methyl-17α-ol-3,20-dione to 19-nor-4,6-pregnadien-6-methyl-17α-ol-3,20-dione 10β-carboxylic acid is complete in approximately 2 days.

(D) Recovery and Decarboxylation Procedure

The whole beer at harvest, from five 100-mL fermentations, is extracted with 250 mL methylene chloride by adjusting the pH downward to 4. The spent beer is re-extracted with another 200 mL methylene chloride. The rich methylene chloride extracts are recovered by centrifugation and then pooled, polished and concentrated to about 50 mL by evaporation. The product, 19-nor-4,6-pregnadien-6-methyl-17α-ol-3,20-dione 10β-carboxylic acid, is then extracted into 50 mL water by adjusting the pH upward to 9. This rich aqueous is diluted with 50 mL methanol, and the pH is adjusted downward to 4. A crude product is crystallized by evaporation of the methanol. The solids are recovered from the aqueous slurry by filtration, washed with 15 mL water, and dried to give 1.22 g of crude crystalline 19-nor-4,6-pregnadien-6-methyl-17α-ol-3,20-dione 10β-carboxylic acid.

1.22 g crude 19-nor-4,6-pregnadien-6-methyl-17α-ol-3,20-dione 10β-carboxylic acid is dissolved in 4 mL methanol, containing 0.1 mL 85% phosphoric acid, and the reaction mixture is heated to 55° C. The reaction mixture is assayed on an hourly basis for 19-nor 4,6-pregnadien-6-methyl-17α-ol-3,20-dione using HPLC. Five microliters of the reaction mixture is diluted into 1 mL acetonitrile and 5 μL injected onto an HPLC column. Conditions for HPLC are as described above. Decarboxylation of 19-nor-4,6-pregnadien-6-methyl-17α-ol-3,20-dione 10β-carboxylic acid to 19-nor 4,6-pregnadien-6-methyl-17α-ol-3,20-dione is complete in approximately 4 hours. The reaction mixture is cooled to -10° C. and crystals are filtered and washed with 1 mL -10° C. methanol to yield 0.72 g of 99.4% pure 19-nor 4,6-pregnadien-6-methyl-17α-ol-3,20-dione.

Example 2

Conversion of 4,6-pregnadien-6-methyl-17α-ol-3,20-dione to 19-nor-4,6-pregnadien-6-methyl-17α-ol-3,20-dione 10β-carboxylic acid is performed using a submerged culture of *Nigrospora gorlenkoanum* ATCC 24718, followed by decarboxylation to 19-nor 4,6-pregnadien-6-methyl-17α-ol-3,20-dione.

Under the conditions described in EXAMPLE 1, 1.18 g of crude crystalline 19-nor-4,6-pregnadien-6-methyl-17α-ol-3,20-dione 10β-carboxylic acid are made. This material is then converted to 0.75 g of 99.7% pure 19-nor 4,6-pregnadien-6-methyl-17α-ol-3,20-dione.

Example 3

Conversion of 4,6-pregnadien-6-methyl-17α-ol-3,20-dione to 19-nor-4,6-pregnadien-6-methyl-17α-ol-3,20-dione 10β-carboxylic acid is performed using a submerged culture of *Nigrospora oryzae* ATCC 42775, followed by decarboxylation to 19-nor 4,6-pregnadien-6-methyl-17α-ol-3,20-dione.

Under the conditions described in EXAMPLE 1, 1.20 g of crude crystalline 19-nor-4,6-pregnadien-6-methyl-17α-ol-3,20-dione 10β-carboxylic acid are made. This material is then converted to 0.65 g of 99.2% pure 19-nor 4,6-pregnadien-6-methyl-17α-ol-3,20-dione.

We claim:

1. A process for the production of a 19-nor-10β-carboxylic acid of Formula II

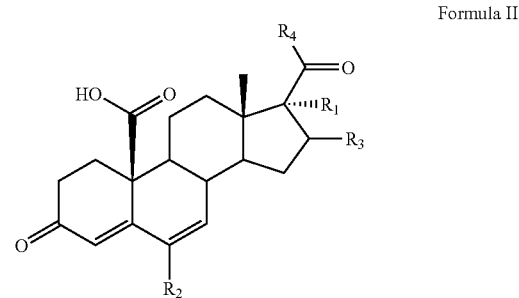

Formula II wherein:
$R_1$ is selected from the group consisting of H, OH, R—C(O)O—, $CH_2OCH_3$, and $CH_3CH(OR)O$—;
R is a $C_1$-$C_8$ alkyl group;
$R_2$ is selected from H, F, Cl, Br, and $CH_3$—;
$R_3$ is H;
$R_4$ is —$CH_2OH$ or —$CH_3$,
by fungal oxidation of a 6-substituted-Δ6-pregnane of Formula I

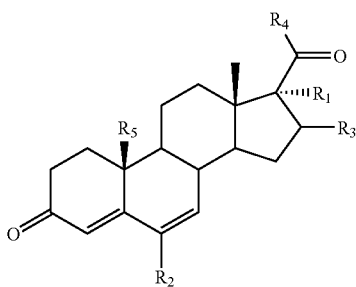

Formula I wherein
$R_1$ is selected from the group consisting of H, OH, R—C(O)O—, $CH_2OCH_3$, and $CH_3CH(OR)O$—;
R is a $C_1$-$C_8$ alkyl group;
$R_2$ is selected from H, F, Cl, Br, and $CH_3$—;
$R_3$ is H;
$R_4$ is —$CH_2OH$ or —$CH_3$,
$R_5$ is —CHO, —$CH_2OH$ or $CH_3$
comprising:
contacting a 6-substituted-Δ6-pregnane of Formula I with a bioconversion medium containing a species of the genus *Nigrospora* capable of oxidizing the 19 carbon of a 6-substituted-$\Delta^6$-pregnane of Formula I, wherein the bioconversion medium contains about 0.1 mL/L to about 4 mL/L of a non-ionic detergent and about 5 g/L to about 60 g/L of a carbon source selected from the groups consisting of monosaccharides, disaccharides, trisaccharides, hydrolyzed polysaccharides, and sugar alcohols, wherein the 6-substituted-Δ6-pregnane is present in the bioconversion medium at a concentration of greater than about 4 g/L.

2. A process according to claim 1 wherein the species of the genus *Nigrospora* is selected from *Nigrospora sphaerica* ATCC 12772, *Nigrospora gorlenkoanum* ATCC 24718, and *Nigrospora oryzae* ATCC 42775.

3. A process according to claim 2 wherein the species of genus i *Nigrospora* is *Nigrospora sphaerica* ATCC 12772.

4. A process according to claim 2 wherein the species of genus *Nigrospora* is *Nigrospora gorlenkoanum* ATCC 24718.

5. A process according to claim 2 wherein the species of genus *Nigrospora* is *Nigrospora oryzae* ATTC 42775.

6. A process according to claim 1 wherein $R_5$ is —CHO.

7. A process according to claim 1 wherein $R_5$ is —$CH_2OH$.

8. A process according to claim 1 wherein $R_5$ is $CH_3$.

9. A process according to claim 1 further comprising the steps of: recovering the compound of Formula II from the bioconversion medium, and decarboxylating the recovered compound of Formula II to form a 19-nor-6-substituted-$\Delta^6$-pregnane of Formula III

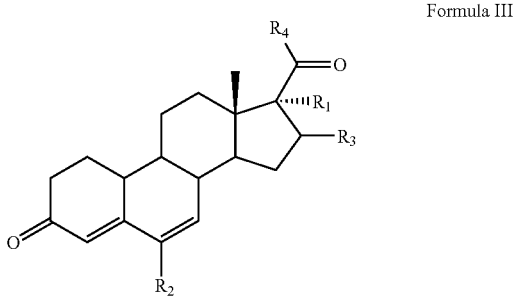

Formula III wherein
$R_1$ is selected from the group consisting of H, OH, R—C(O)O—, $CH_2OCH_3$, and $CH_3CH(OR)O$—;
R is a $C_1$-$C_8$ alkyl group;
$R_2$ is selected from H, F, Cl, Br, and $CH_3$—;
$R_3$ is H;
$R_4$ is —$CH_2OH$ or —$CH_3$,
$R_5$ is —CHO, —$CH_2OH$ or $CH_3$,
comprising the step of treating the compound of Formula II with an acid of pKa less than 4.9 in a suitable solvent.

10. A process according to claim 6 in which the acid of pKa less than 4.9 is hydrochloric acid and the suitable solvent is methanol.

11. A process according to claim 1 wherein the carbon source is glucose.

* * * * *